United States Patent [19]

Heinonen et al.

[11] Patent Number: 5,799,711
[45] Date of Patent: Sep. 1, 1998

[54] ARRANGEMENT IN CONNECTION WITH AN ANAESTHETIC LIQUID CONTAINER

[75] Inventors: Erkki Heinonen, Helsinki; Antti Särelä, Espoo; Jukka Kankkunen, Vantaa, all of Finland

[73] Assignee: Instrumentarium Oy, Helsinki, Finland

[21] Appl. No.: 773,431

[22] Filed: Dec. 27, 1996

[30] Foreign Application Priority Data

Dec. 29, 1995 [FI] Finland ................... 956354
Apr. 18, 1996 [FI] Finland ................... 961698
Dec. 11, 1996 [FI] Finland ................... 964966

[51] Int. Cl.⁶ ................................. B65B 1/04
[52] U.S. Cl. .................. 141/18; 141/59; 141/198; 141/364; 141/320; 141/290; 128/200.19
[58] Field of Search .................. 141/2, 18, 21, 141/45, 59, 61, 198, 285, 286, 289, 290, 291, 292, 293, 295, 308, 309, 346–352, 363–366, 311 A, 319–321, 353–355, 357, 382, 115–120; 128/200.19, 200.16, 200.21; 137/207.5

[56] References Cited

U.S. PATENT DOCUMENTS

| | | | |
|---|---|---|---|
| 3,530,905 | 9/1970 | Drager | 141/18 |
| 3,565,133 | 2/1971 | Jones . | |
| 4,867,212 | 9/1989 | Mohr et al. | 141/290 |
| 5,381,836 | 1/1995 | Braatz et al. . | |
| 5,505,236 | 4/1996 | Grabenkort et al. . | |

FOREIGN PATENT DOCUMENTS

| | | |
|---|---|---|
| 448954 | 10/1991 | European Pat. Off. . |
| 578513 | 1/1994 | European Pat. Off. . |
| 503164 | 4/1996 | Sweden . |
| 2252962 | 8/1992 | United Kingdom . |
| 4106756 | 9/1992 | United Kingdom . |
| 2279016 | 12/1994 | United Kingdom . |
| 95/11717 | 5/1995 | WIPO . |
| 95/18644 | 7/1995 | WIPO . |

OTHER PUBLICATIONS

European Standard prEN 1280–1, Oct. 1996.

*Primary Examiner*—J. Casimer Jacyna
*Assistant Examiner*—Steven O. Douglas
*Attorney, Agent, or Firm*—Andrus, Sceales, Starke & Sawall

[57] ABSTRACT

An arrangement in connection with an anaesthetic liquid container, comprising a connector with the help of which an anaesthetic liquid container and a transport or supply container of anaesthetic liquid can be connected to one another for guiding the anaesthetic liquid from the transport or supply container to the anaesthetic liquid container and for removing a volume of gas equivalent to the anaesthetic liquid from the anaesthetic liquid container to the transport or supply container. In order to provide a reliable and tight connection, the connector comprises a conduit arrangement which, when connecting the anaesthetic liquid container and the transport or supply container to one another, is adapted to open first a flow connection exclusively to gas.

5 Claims, 2 Drawing Sheets

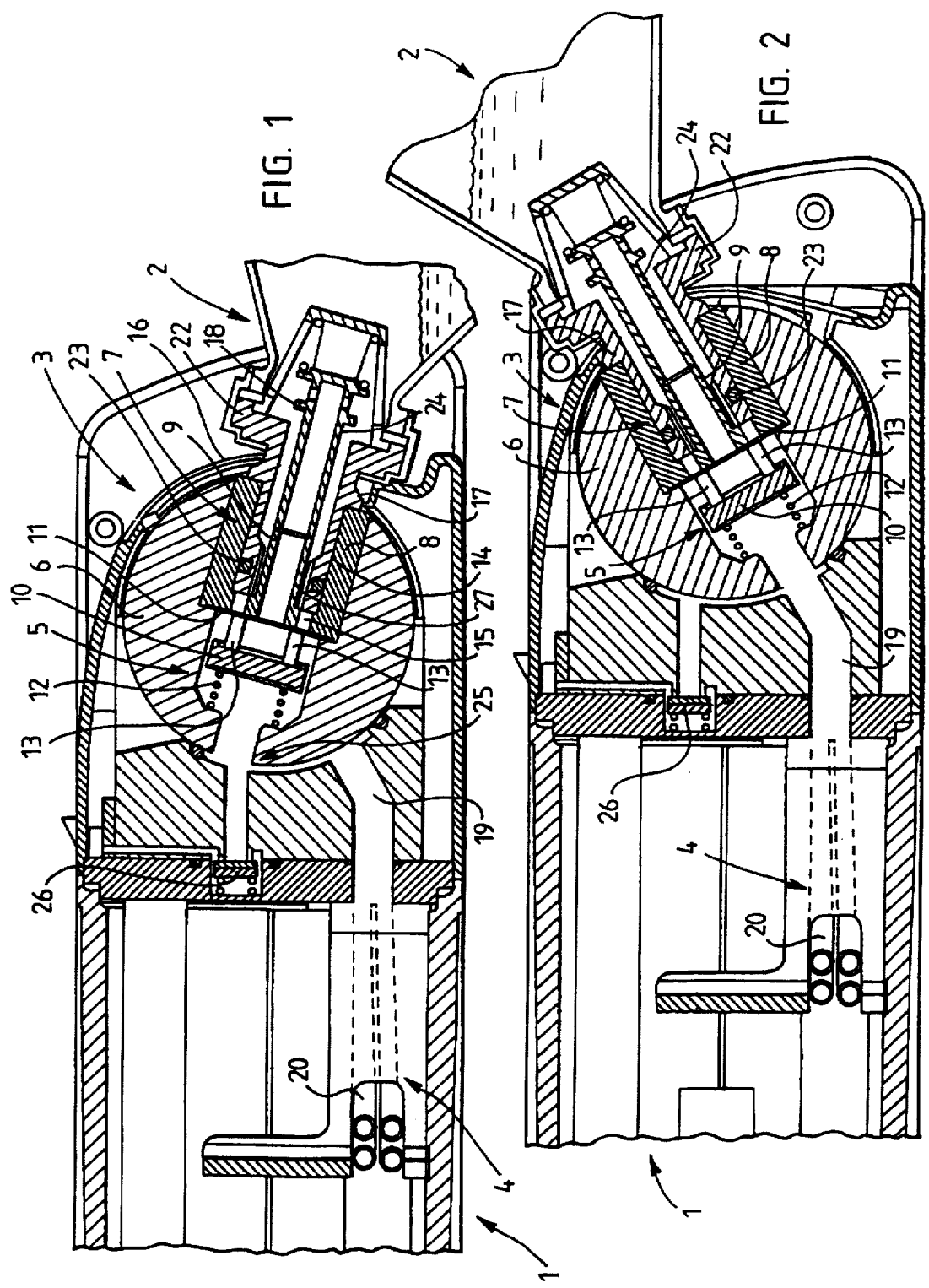

ARRANGEMENT IN CONNECTION WITH AN ANAESTHETIC LIQUID CONTAINER

BACKGROUND OF THE INVENTION—FIELD OF THE INVENTION

Arrangement in connection with an anaesthetic liquid container

The present invention relates to an arrangement in connection with an anaesthetic liquid container, comprising connection means with the help of which an anaesthetic liquid container and a transport or supply container of anaesthetic liquid can be connected to one another for guiding anaesthetic liquid from the transport or supply container to the anaesthetic liquid container and for removing a volume of gas equivalent to the anaesthetic liquid from the anaesthetic liquid container to the transport or supply container.

BACKGROUND OF THE INVENTION—DESCRIPTION OF THE RELATED ART

The arrangements described above are fairly well known in connection with anaesthesia apparatuses. Several different solutions are known in the field. Differences in the filling mechanisms are caused e.g. by restrictions and requirements set by the operational principle or the liquid of the vaporizer.

It is a common requirement for all state of the art filling methods that the anaesthetic liquid has to be sufficiently isolated from the atmosphere during the filling process. If this is not the case, the anaesthetic agents, which have a strong smell and evaporate easily, will contaminate the atmosphere of the vaporizer very fast. In order to limit the contamination effect described above, existing device standard drafts, e.g. in prEN 1280, have determined how much anaesthetic liquid may evaporate into the atmosphere during filling. A closed filling system is required in most cases in order to fulfil this requirement.

In an anaesthetic vaporizer operating on the bypass-saturation principle, the anaesthetic agent content of gas administered to the patient is regulated by regulating the inflow ratio of gas flows passing by and passing through the liquid container. A requirement for the appropriate operation of this kind of a vaporizer is that the amount of liquid in the liquid container will not exceed the allowable level. If the level should be exceeded, the liquid might block the flow conduit which passes through the liquid container and carries the gas flow to be supplied to the patient. The gas flow may, however, pressurize the liquid container, forcing the excess liquid out to the gas flow conduit passing to the patient, which results in a serious risk of overdosage. In order to limit the amount of liquid, vaporizers are provided with a device which prevents them from being filled over the maximum allowable amount of liquid.

In a closed filling system, the filling of an anaesthetic liquid container is based on the exchange of volumes between a liquid container and a transport or supply container. A transport or supply container is often referred to in the field as a bottle. When liquid flows from the bottle to the anaesthetic liquid container, an equivalent amount of gas flows from the liquid container to the bottle. The filling of the liquid container will stop in case either liquid or gas flow is exhausted, or in case both of the flows are exhausted.

In order to keep the filling system closed, most known solutions are provided with a bottle containing a cut-off valve. This kind of a system also comprises a vaporizer which contains a connector for fixing the bottle tight to the vaporizer, a flow conduit between the connector and the liquid container, and a cut-off valve in the flow conduit. In the system the bottle is first placed in the connector of the vaporizer and after this the valves will open in the order depending on different embodiments. Similarly, when the filling is terminated, the valve will close in the order depending on the embodiment before the bottle is detached from the connector of the vaporizer.

There are in use two different types of bottles containing a cut-off valve. The system described in U.S. Pat. 5,505,236 is intended for anaesthetic liquids whose boiling points are high with respect to the temperature in the ambient atmosphere. The solution described in the patent is only half-closed as gas, which passes before liquid from the liquid container, flows out from the system and the bottle receives the replacement gas from the vent in the juncture of the connector of the vaporizer and the bottle. In the solution the bottle includes a cut-off valve in the immediate vicinity of the mouth of the bottle. The bottle is disposed in the connector of the vaporizer with the mouth downwards. The bottle is pressed to the connector of the vaporizer. As the bottle is pressed even deeper, the cut-off valve of the vaporizer will open. When pressed further, the valve of the bottle will open, thus enabling flows between the liquid container and the bottle. Similarly, when the bottle is detached from the vaporizer, the valve of the bottle will close first, whereby the flow of liquid possibly still in the bottle will cease. When the cut-off valve of the vaporizer is still open, the liquid still in the space between the valves is able to flow into the vaporizer, provided that the vaporizer is not yet full. Further, when the bottle is being detached, the cut-off valve of the vaporizer will close and after this the bottle will be detached from the vaporizer. In case in the solution described above the filling has stopped by means of a system preventing overfilling, that is, when the vaporizer becomes full, anaesthetic agent will remain in the space between the bottle and the cut-off valves of the vaporizer. This liquid will either evaporate to the atmosphere, or in case the vaporizer is provided with a tight cap, it will remain in the space between the cap and the vaporizer until the next filling time.

There are considerable shortcomings and limitations in the solution. Liquid splashes may be released from the vent of the bottle if the bottle is moved during filling or after it. On the other hand, gas removing from the vaporizer contains a great amount of anaesthetic vapour which has to be passed to the degassing system if said contamination of the ambient atmosphere is to be avoided. Furthermore, the system preventing overfilling described in the reference cited has been adapted to operate only in the normal position of use of the vaporizer. Overfilling is possible by inclining the vaporizer. The system is also susceptible to misuse, for example to manual opening of said cut-off valves in situations where the bottle is not coupled to the connector of the vaporizer. The bottle valve is small in size and the pressure in the bottle is small, wherefore it will cause no great disadvantage, and also, the bottle is provided with a screw cap which will eliminate that a valve of this kind should be opened inadvertently. Manual opening of the cut-off valve during the use of the vaporizer will cause the pressure in the vaporizer and the gas intended for the patient to be released through the filling connector to the atmosphere. The screw cap in the vaporizer can eliminate this kind of a situation from being developed inadvertently. The caps, however, make the solution to some degree difficult to use. If the vaporizer is attempted to be filled contrary to instructions when evaporation is under way, it will result in that after the cut-off valve has been opened, the pressure in the vaporizer will be released through the vent of the bottle to the atmosphere.

U.S. Pat. No. 5,381,836 discloses a solution similar to the embodiment discussed above. The primary difference to the embodiment shown above is that the arrangement is also suitable for liquids whose boiling point are close to the ambient temperature and even below it, which means that there may be even a significantly great pressure in the bottle which, when released to the atmosphere, may cause rapidly the contamination of a vast area. In this kind of an embodiment the filling system has to be closed, in which case all the flows take place between the bottle and the liquid container. For this purpose, there has to be a sealing member between the mouth of the bottle and the connecting means of the vaporizer. The other required actuators are the same as above, that is, a cut-off valve of the bottle, a connecting means, a liquid container and a cut-off valve of the vaporizer and a flow conduit connecting the connecting means and the liquid container. The connecting means of the vaporizer is positioned in a circular conduit so that the bottle can be mounted and removed from the connecting means only when its mouth is positioned downwards. When the vaporizer is being filled, the bottle is first pressed against the connecting means of the vaporizer, whereby a sealed connection is formed between them. When pressed further, the cut-off valve of the bottle opens and the bottle settles into a position which will enable the connecting means of the vaporizer to be turned to the upper position. In that case the bottle is also locked to the connecting means and the mouth of the bottle is turned downwards. This turning movement causes the cut-off valve of the vaporizer to open, whereby flows are possible between the bottle and the liquid container. Correspondingly, when filling is terminated, the connecting means of the vaporizer and the bottle are turned downwards first. This turning causes the cut-off valve of the vaporizer to close. When the mouth of the bottle is upwards, the liquid possibly remaining in the space between the valves flows back to the bottle. The valve of the bottle closes when the bottle is pulled outwards from the connecting means. The seal of the bottle opens last from the connecting means of the vaporizer.

As there may be a great pressure in the anaesthetic liquid bottle, particular attention has been paid to the protection of the cut-off valve of the bottle in case of misuse. The valve is situated deep in the bottle far from the spout of the bottle. It is impossible to operate the valve without tools. This provides the disadvantage that a great volume of very volatile liquid may remain between the bottle and the cut-off valves of the vaporizer if the vaporizer is full before the bottle is empty. It is therefore necessary to provide the vaporizer with a turning device. There may be an overpressure of about 2 bar in the vaporizer during use. Therefore it is very important for reasons of safety that the cut-off valve of the vaporizer is positioned so that it cannot be opened inadvertently without the bottle being in place. In the case of the reference cited this is prevented by that the cut-off valve of the vaporizer is situated on the periphery of the rotating cylinder and to effect the rotating movement, the bottle must be mounted in place, in which case the catch stopping the rotation is moved from out of the way. As an advantage of the bottle being locked is also mentioned that when the cut-off valve of the vaporizer is opened, the internal pressure of the vaporizer will be directed to the bottle and causes a risk that the bottle will get detached from the filling device. On the one hand, this risks will remain after filling when the cut-off valve of the vaporizer is already closed and when the bottle is lowered to the lower position. The pressure prevailing in the system will remain in the conduit after filling, the pressure being still directed to the bottle. On the other hand, when the mouth of the bottle is upwards and the cut-off valve of the bottle closes immediately, there is very little risk of leakage. In addition to the cut-off valve of the actual primary vaporizer, the patent includes a description of another cut-off valve of the vaporizer which opens when the bottle is mounted in the connecting means of the vaporizer. Because of the reasons mentioned above, this is not sufficient in the solution of the patent. Notwithstanding the ease of use when both of the cut-off valves open simultaneously, there is no actual advantage of the presence of another valve. Not even this advantage has been utilized in the solution as a turning movement is still required for filling the liquid container. The solution shown in the U.S. patent does not either contain a solution for preventing overfill of a bypass-saturation type of vaporizer in a situation where the vaporizer is inclined.

The solution of aforementioned U.S. Pat. No. 5,381,836 has been improved by a solution described in Swedish Patent 503,164. In the solution according to the reference cited, the cut-off valve of the vaporizer has been protected against inadvertent opening when the bottle is not coupled in place. This is realized in such a manner that the moving piston in the connecting means of the vaporizer described in U.S. Pat. No. 5,381,836, in which the movement of the secondary cut-off valve is coupled to the movement of the piston and which piston also causes the cut-off valve of the bottle to open, is replaced by a pin attached to the vaporizer and detached pins coupled to the cut-off valves of the vaporizer. These pins are situated deep in the filling device of the vaporizer inside a tubular connector body in a narrow annular space between said body and an opening element. To open the cut-off valve of the vaporizer without the bottle being locked in place would require the pins to be pressed, which would be impossible to be done inadvertently without tools in the geometry of the described solution.

SUMMARY OF THE INVENTION

The object of the invention is to provide an arrangement by means of which the drawbacks of prior art can be eliminated. This has been achieved with the arrangement of the invention that is characterized in that the connecting means comprise a conduit arrangement which, when connecting the anaesthetic liquid container and the transport or supply container to one another, is adapted to open first a flow connection exclusively to gas.

The primary advantage of the invention is that the solution is suitable for filling methods of such anaesthetic liquids for a bypass-saturation vaporizer whose boiling points are close to or even below the ambient temperature. A further advantage of the invention is also its simplicity in comparison with prior art solutions. The invention is also suited to be used in connection with mechanisms preventing overfill.

BRIEF DESCRIPTION OF THE DRAWING

In the following, the invention will be described in greater detail by means of the preferred embodiment illustrated in the accompanying drawings, in which FIG. 1 shows the arrangement of the invention at an initial stage of filling an anaesthetic liquid container, FIG. 2 shows the arrangement of FIG. 1 at a later stage of filling an anaesthetic liquid container.

DESCRIPTION OF THE PREFERRED EMBODIMENT

Figure 3:
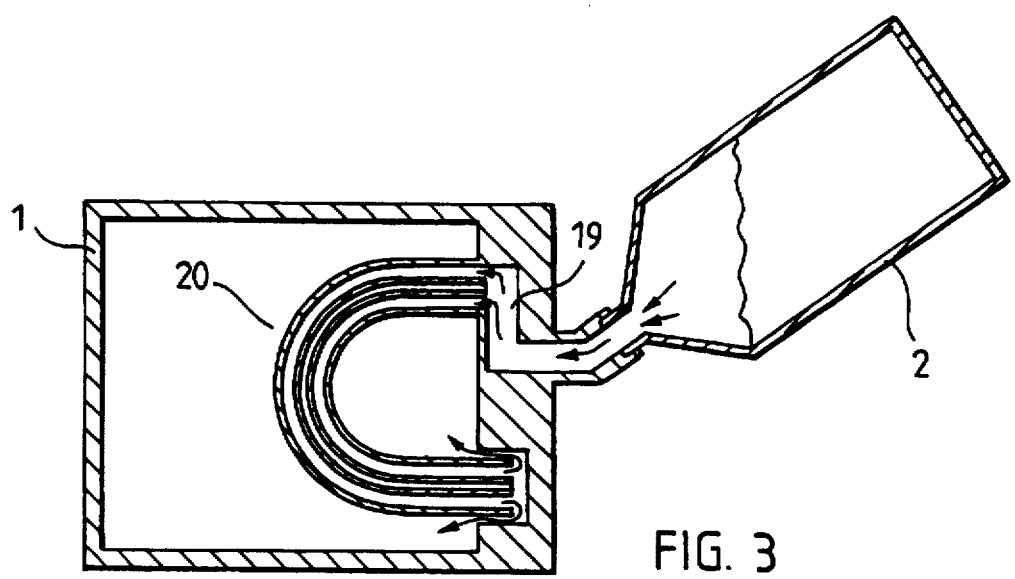
FIG. 3 shows a schematic top view of the arrangement of FIGS. 1 and 2.

In the examples of the figures reference numeral 1 generally denotes an anaesthetic liquid container and reference numeral 2 a transport or supply container of anaesthetic liquid which is also referred to in the field as a bottle. The arrangement also comprises connecting means with the help of which the anaesthetic liquid container 1 and the transport or supply container 2 of anaesthetic liquid can be connected to one another for guiding anaesthetic liquid from the transport or supply container 2 of anaesthetic liquid to the anaesthetic liquid container 1 and for removing an amount of gas equivalent to the filling of anaesthetic liquid from the anaesthetic liquid container 1 to the transport or supply container 2. The connecting means are generally indicated in the figures with reference numeral 3. The arrangement also comprises means 4 which are adapted to cut off the flow of the anaesthetic liquid to the anaesthetic liquid container 1 at the predetermined surface level.

According to the essential idea of the invention, the connecting means 3 comprise a conduit arrangement 5 which is adapted, when connecting the anaesthetic liquid container 1 and the transport or supply container 2 to one another, to open first a flow connection exclusively to gas. The conduit arrangement 5 described above may be preferably formed into an essentially cylindrical portion 6 which is provided with connecting parts 7 for the transport or supply container 2. The cylindrical portion 6 is adapted to be turned around its longitudinal axis between two positions in such a manner that a flow connection exclusively to gas opens in the first position of the cylindrical portion, shown in FIG. 1, and a second flow connection, which enables the flow of the anaesthetic liquid, only in the second position of the cylindrical portion 6, shown in FIG. 2.

As was stated above, the preferred embodiment of the arrangement comprises an essentially cylindrical, rotating portion 6 to which a tubular connector 8 of the vaporizer is adapted. The connector has a fixed centre pin 9 and a moving cut-off valve 10. This valve is sealed in the connector against an abutment surface 11 on one hand by means of the pressure in the liquid container 1 and the flow conduit and on the other hand by means of a spring 12. The cut-off valve has one or more fixedly mounted pins 13. These pins extend inside the connector 8 to an annular space 15 confined by an inner surface 14 of the connector and the centre pin. The cut-off valve 10 will open when the pins 13 are pressed. Because of the geometry of the construction, it is impossible to press the pins inadvertently.

In order to make it easier to operate the turning cylindrical portion 6 and to prevent the bottle 2 from being detached inadvertently, the vaporizer also has a locking mechanism which retains the bottle in place during turning. In the solution of the figures, locking takes place in a groove whose edges 16 are locked around a collar 17 in the bottle 2. In order to empty the volume remaining between a cut-off valve 18 of the bottle 2 and the cut-off valve of the vaporizer after use, it is also advantageous for the locking mechanism that the bottle 2 can be placed in the connector only when the mouth of the bottle is upwards, that is, when the connector of the vaporizer is downwards, cf. FIG. 1. There is a connecting conduit 19 between the connector of the vaporizer and the liquid container 1 for enabling flows between the bottle 2 and the liquid container. The connecting conduit thus forms a common conduit for anaesthetic liquid and gas. The connecting conduit comprises an intermediate container 20 which can preferably be a device formed by a curved portion described in Finnish Patent Application 961,698, which device stops flowing immediately when the liquid container is inclined during filling into a position where its overfilling would be possible. The intermediate container 20 formed by a curved tubular portion can be seen clearly in FIG. 3. The intermediate container 20 may be formed from one or more curved tubes. The curved tubes need not necessarily be U-shaped tubes as shown in the figure, but the curved shape can also be provided by means of a tube that turns stepwise and so on. FIG. 3 shows a schematic view of a situation where the flowing of liquid to the container 1 has stopped. The intermediate container described above is based on the common flow conduit of liquid and gas flow contained in the intermediate container. The intermediate container comprises a liquid flow outlet level (liquid threshold) and a gas flow outlet level (gas threshold). The flowing of liquid from the bottle to the vaporizer is possible only when the liquid threshold is situated below the gas threshold. Otherwise the intermediate container fills with liquid until the liquid level reaches the gas threshold. Then the replacement gas flow to the bottle is cut off and the filling stops. The intermediate container is mounted in the vaporizer so that the liquid threshold is in the allowable filling position below the gas threshold and rises above it when the vaporizer is turned into a position where filling is not allowed. The operation of the solution requires a totally closed filling system.

To fill the liquid container 1 from the bottle 2, a filling head 22 attached fixedly to the bottle is placed in the connector of the vaporizer. At first, the bottle is sealed into the filling head, thus forming a closed filling system by means of a seal 23 either in the connector of the vaporizer or, as when using a specific bottle, in the filling head 22. When the filling head 22 is transferred even deeper into the connector, the centre pin 9 of the connector contacts a centre pin 24 coupled to the cut-off valve 18 of the bottle, inside the filling head 22. When the transferring movement continues, the cut-off valve of the bottle will open, after which the filling head will contact the pins 13 coupled to the cut-off valve of the vaporizer. Further, when the movement is continued, the filling head 22 opens the cut-off valve 10 of the vaporizer by means of the pins 13. Now the flow conduit between the bottle and the liquid container is open. As the bottle 2 is still in the lower position, FIG. 1, and a threshold 25 connected to the flow conduit is above the liquid level of the bottle, only the gas flow between the bottle and the anaesthetic liquid container of the vaporizer is possible. An overpressure valve in this flow connection is indicated with reference numeral 26 in the figures. The gas flow in question balances effectively the possible pressure difference between the bottle and the vaporizer before the bottle is turned into the upper position as in FIG. 2, where the liquid flow is also possible. This pressure balancing is advantageous in such an exceptional case that an already full liquid container is to be filled from a significantly warmer bottle than the liquid container. If pressure balancing is not performed by the exchange of gas before filling is started, it will take place by the liquid flow during filling. As the liquid flow does not require in such a case a replacement gas flow from the liquid container to the bottle, this may result in overfilling.

When the bottle is in the lower position, FIG. 1, the overpressure in the vaporizer is directed to the bottle when the cut-off valve 10 opens and presses the bottle outwards. In this case the user is, however, actively pressing the bottle inwards so that there is no risk of leakage. On the other hand, although this pressure should surprise the user, in the worst case it will result in the bottle moving outwards until the cut-off valve 10 is closed again. However, if this risk is to be completely eliminated, the moving of the filling head 22 directed inwards to the connector of the vaporizer may be carried out by means of a thread 27 arranged in the filling head by providing the pin 9 with a similar external thread. In this case the bottle is locked in place even before the cut-off valve of the vaporizer is opened. When the filling head 22 is at the bottom in the connector of the vaporizer, the collar 17 of the filling head is in place in such a manner that the edges 16 of the groove in the vaporizer will remain between the bottle and the collar 17, thus retaining the bottle locked in place. The filling of the liquid container continues when the bottle is in the upper position as long as the liquid is able to flow from the bottle to the liquid container and the replacement gas from the liquid container to the bottle. This flow will be cut off if the liquid threshold in the flow conduit system will rise above the gas threshold or if the liquid is emptied from the bottle. When the filling is terminated, the bottle is detached by turning it first to the lower position, whereby the liquid in the space between the cut-off valves is able to flow back to the bottle. When the bottle is in the lower position, the edges 16 of the groove in the vaporizer also release the collar 17 of the filling head, thus making it possible to move the bottle outwards. During moving, the cut-off valve 10 of the vaporizer will close first and then the cut-off valve 18 of the bottle. The seal between the filling head 22 and the connector of the vaporizer will open last. The only leakage to the atmosphere during filling is the gas in the space between the cut-off valves. To minimize even this leakage, it is advantageous to minimize the volume in question although within the framework of other boundary conditions.

The embodiment described above is in no way intended to limit the invention, but the invention may be modified fully freely within the scope of the appended claims. It will therefore be clear that the arrangement of the invention or its details need not be precisely as shown in the figures, but other solutions are also possible.

We claim:

1. An arrangement for connecting an anaesthetic supply container to an anaesthetic liquid container of a vaporizer for supplying a quantity of liquid anaesthetic from the anaesthetic supply container to the anaesthetic liquid container and for removing a volume of gas from the anaesthetic liquid container to the anaesthetic supply container, said arrangement comprising:

mean for establishing an anaesthetic liquid level in the anaesthetic liquid container; and connecting means mounted in the vaporizer for connecting the anaesthetic supply container to the anaesthetic liquid container, said connecting means being movable with respect to the vaporizer to orient the anaesthetic supply container to upper and lower positions with respect to the vaporizer, the anaesthetic supply container being receivable in said connecting means only when said connecting means is in said lower position, said connecting means providing a fluid flow conduit between the anaesthetic supply container and the anaesthetic liquid container that is open in both said positions when the anaesthetic supply container is connected to the anaesthetic liquid container, said fluid flow conduit having a first end in fluid communication with the anaesthetic liquid container and a second end in fluid communication with the anaesthetic supply container, said first end of said fluid flow conduit being positioned above the anaesthetic liquid level in the anaesthetic liquid container and the second end of said fluid flow conduit being positioned above the level of liquid anaesthetic in the anaesthetic supply container when said connecting means is moved to position the anaesthetic supply container in the lower position so that initially only gas flows through said fluid flow conduit when the anaesthetic supply container is received in said connecting means to balance the gas pressures in the anaesthetic supply container and the anaesthetic liquid container, the anaesthetic supply container thereafter supplying anaesthetic to the anaesthetic liquid container through said fluid flow conduit when said connecting means is moved to position the anaesthetic supply container is said upper position.

2. The arrangement according to claim 1 wherein said connecting means comprises a cylindrical member having an axis of rotation, said fluid flow conduit extending through said cylindrical member transverse to said axis of rotation, said cylindrical member being arcuately movable about said axis of rotation to orient the anaesthetic supply container in said first and second positions.

3. The arrangement according to claim 2 wherein said connecting means includes locking means by which the anaesthetic supply container can be coupled to said connecting means only when said connecting means is in said lower position.

4. The arrangement according to claim 1 wherein said connecting means includes locking means by which the anaesthetic supply container can be coupled to said connecting means only when said connecting means is in said lower position.

5. The arrangement according to claim 1 wherein said means for establishing the anaesthetic liquid level in the anaesthetic liquid container comprises an intermediate container in fluid communication with said first end of said fluid flow conduit and formed as a curved tubular element.

* * * * *